United States Patent
An et al.

(10) Patent No.: US 9,977,307 B2
(45) Date of Patent: May 22, 2018

(54) TRANSPARENT DISPLAY DEVICE

(71) Applicant: LG DISPLAY CO., LTD., Seoul (KR)

(72) Inventors: Hyun Jin An, Paju-si (KR); Jong Moo Kim, Seoul (KR); Jin Hyun Jung, Seoul (KR)

(73) Assignee: LG DISPLAY CO., LTD., Seoul (KR)

( * ) Notice: Subject to any disclaimer, the term of this patent is extended or adjusted under 35 U.S.C. 154(b) by 0 days. days.

(21) Appl. No.: 15/362,361

(22) Filed: Nov. 28, 2016

(65) Prior Publication Data
US 2017/0192334 A1    Jul. 6, 2017

(30) Foreign Application Priority Data
Dec. 31, 2015  (KR) .................. 10-2015-0191487

(51) Int. Cl.
| | | |
|---|---|---|
| *G02F 1/15* | (2006.01) | |
| *G02F 1/153* | (2006.01) | |
| *G02F 1/163* | (2006.01) | |
| *C07D 213/22* | (2006.01) | |
| *G09G 3/38* | (2006.01) | |
| *C09K 11/06* | (2006.01) | |
| *G02F 1/155* | (2006.01) | |
| *G02F 1/161* | (2006.01) | |
| *G09G 3/34* | (2006.01) | |

(52) U.S. Cl.
CPC ........... *G02F 1/163* (2013.01); *C07D 213/22* (2013.01); *C09K 11/06* (2013.01); *G02F 1/155* (2013.01); *G02F 1/161* (2013.01); *G09G 3/38* (2013.01); *C09K 2211/1044* (2013.01); *G02F 1/15* (2013.01); *G02F 2001/1635* (2013.01); *G02F 2203/01* (2013.01); *G09G 3/34* (2013.01)

(58) Field of Classification Search
CPC .......... G02F 1/15; G02F 1/153; G02F 1/1521; G02F 1/1523; G02F 1/155; G02F 1/161; G02F 1/163; G02F 2001/1552; G02F 2001/1635; G02F 2203/01; C07D 213/22; C09K 11/06; C09K 9/02; C09K 2211/1044; G09G 3/30; G09G 3/34; G09G 3/38; G09G 3/3208; H01L 27/1214; H01L 51/5203
USPC ...... 359/265, 270, 273, 275; 345/76, 77, 84, 345/88, 105, 204, 205, 690; 348/46, 51, 348/E13.001; 313/498, 501, 503; 349/42, 43, 106; 257/88, 89
See application file for complete search history.

(56) References Cited

U.S. PATENT DOCUMENTS

| | | | | |
|---|---|---|---|---|
| 7,463,399 | B2* | 12/2008 | Shin ................... | H01L 27/3232 257/59 |
| 7,719,185 | B2* | 5/2010 | Jin ..................... | H01L 27/3244 313/506 |
| 8,284,242 | B2* | 10/2012 | Wang ................. | H04N 13/0452 348/46 |
| 8,654,431 | B2* | 2/2014 | Chung ................ | G02F 1/15 359/265 |

(Continued)

*Primary Examiner* — Loha Ben
(74) *Attorney, Agent, or Firm* — Dentons US LLP

(57) ABSTRACT

Disclosed is a transparent display device including an electrochromic element. The electrochromic element includes an electrochromic layer, a counter layer, and an electrolyte layer. An image is displayed through an oxidation-reduction reaction, and the display device is in a transparent mode when a voltage is not applied. The electrochromic layer and the counter layer may further include a core material for changing a color at a high speed.

16 Claims, 4 Drawing Sheets

(56) References Cited

U.S. PATENT DOCUMENTS 8,760,606 B2 * 6/2014 Allemand .............. B82Y 10/00
                                                 349/111
9,442,338 B2 * 9/2016 Uhm ....................... G02F 1/155

* cited by examiner

TRANSPARENT DISPLAY DEVICE

CROSS-REFERENCE TO RELATED APPLICATIONS

This application claims the benefit of Korean Patent Application No. 10-2015-0191487 filed on Dec. 31, 2015, which is hereby incorporated by reference as if fully set forth herein.

BACKGROUND

Field of the Invention

The present invention relates to a transparent display device.

Discussion of the Related Art

Recently, as society advances to the information-oriented society, the display field of processing and displaying a massive amount of information is rapidly advancing, and various display devices have been developed and are attracting much attention. The display devices include liquid crystal display (LCD) devices, plasma display panel (PDP) devices, field emission display (FED) devices, electroluminescence display (ELD) devices, and organic light emitting diode (OLED) display devices, etc.

Recently, the display devices are thinned and lightened and are low in consumption power, and thus, the application field of display devices is continuously increasing. Particularly, a display device is used as a user interface in most electronic devices, mobile devices, etc.

Moreover, transparent display devices which enable a user to see a background or an object disposed on a rear surface thereof are being actively researched recently.

FIG. 1 is a plan view illustrating a transmissive area (TA) and a display area (EA) of a related art transparent display device. In this case, the related art transparent display device may be a liquid crystal display device or an organic light emitting display device. The related art transparent display device has the following problems.

When the transparent display device is implemented as the liquid crystal display device, it is hard to realize a transmittance of 15% or more because of transmittance loss by a polarizing film.

When the transparent display device is implemented as the organic light emitting display device, securing of the transmissive area is restricted due to a thin film transistor (TFT), and for example, if the number of TFTs is reduced, it is hard to realize a high resolution. There is a tradeoff relationship between realization of a high resolution and an increase in transmittance caused by securing of the transmissive area.

Therefore, the inventors has invented a transparent display device which realizes a high resolution, has a transmittance of 50% or more in a transparent mode, and changes a color at a high speed.

The above-described background is possessed by the inventor of the application for deriving the invention, or is technology information that has been acquired in deriving the invention. The above-described background is not necessarily known technology disclosed to the general public before the application of the invention.

SUMMARY

Accordingly, the present invention is directed to provide a transparent display device that substantially obviates one or more problems due to limitations and disadvantages of the related art.

An aspect of the present invention is directed to provide a transparent display device which realizes a high resolution in a display mode.

Another aspect of the present invention is directed to provide a transparent display device which realizes a transmittance of 50% or more in a transparent mode.

Additional advantages and features of the invention will be set forth in part in the description which follows and in part will become apparent to those having ordinary skill in the art upon examination of the following or may be learned from practice of the invention. The objectives and other advantages of the invention may be realized and attained by the structure particularly pointed out in the written description and claims hereof as well as the appended drawings.

To achieve these and other advantages and in accordance with the purpose of the invention, as embodied and broadly described herein, there is provided a transparent display device that includes a first substrate and a second substrate facing each other, a thin film transistor (TFT) disposed on one surface of the first substrate, a first transparent electrode connected to the TFT, a second transparent electrode disposed on the second substrate to face the first substrate, and an electrochromic element provided between the first transparent electrode and the second transparent electrode.

It is to be understood that both the foregoing general description and the following detailed description of the present invention are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this application, illustrate embodiments of the invention and together with the description serve to explain the principle of the invention. In the drawings.

DETAILED DESCRIPTION OF THE INVENTION

Figure 1:
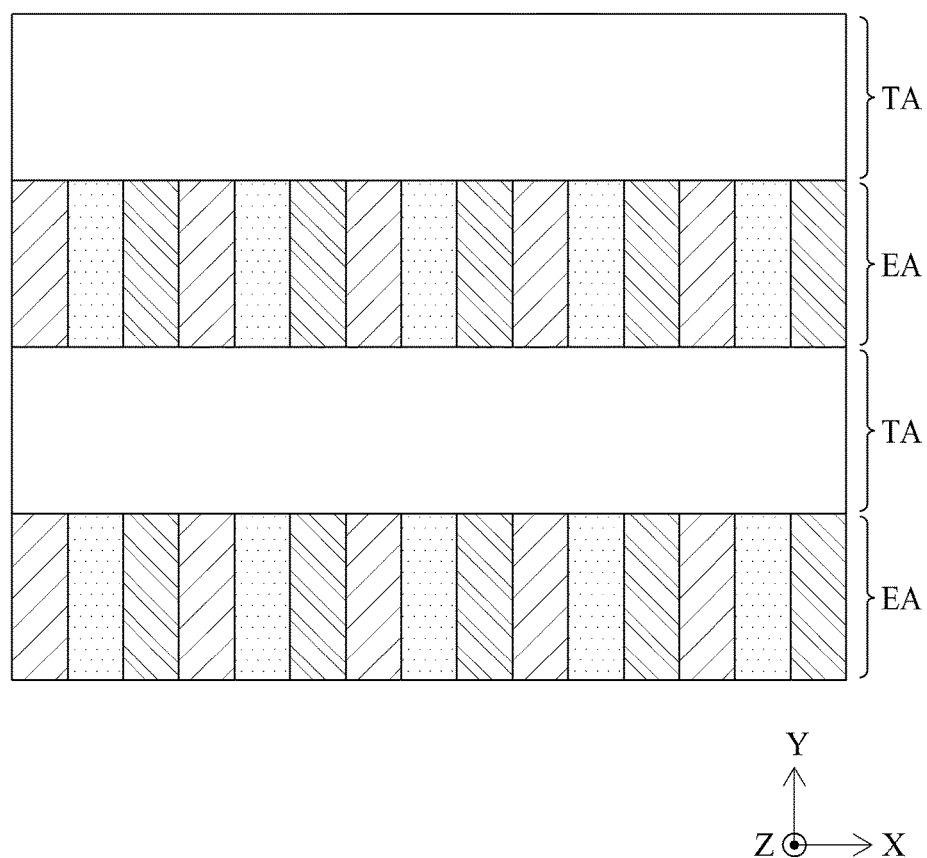
FIG. 1 is a plan view of a related art transparent display device.

Reference will now be made in detail to the exemplary embodiments of the present invention, examples of which are illustrated in the accompanying drawings. Wherever possible, the same reference numbers will be used throughout the drawings to refer to the same or like parts.

Advantages and features of the present invention, and implementation methods thereof will be clarified through following embodiments described with reference to the accompanying drawings. The present invention may, however, be embodied in different forms and should not be construed as limited to the embodiments set forth herein. Rather, these embodiments are provided so that this disclosure will be thorough and complete, and will fully convey the scope of the present invention to those skilled in the art. Further, the present invention is only defined by scopes of claims.

A shape, a size, a ratio, an angle, and a number disclosed in the drawings for describing embodiments of the present invention are merely an example, and thus, the present invention is not limited to the illustrated details. Like reference numerals refer to like elements throughout. In the following description, when the detailed description of the relevant known function or configuration is determined to unnecessarily obscure the important point of the present invention, the detailed description will be omitted. In a case where 'comprise', 'have', and 'include' described in the present specification are used, another part may be added unless 'only~' is used. The terms of a singular form may include plural forms unless referred to the contrary.

In construing an element, the element is construed as including an error range although there is no explicit description.

In describing a position relationship, for example, when a position relation between two parts is described as 'on~', 'over~', 'under~' and 'next~', one or more other parts may be disposed between the two parts unless 'just' or 'direct' is used.

In describing a time relationship, for example, when the temporal order is described as 'after~', 'subsequent~', 'next~', and 'before~', a case which is not continuous may be included unless 'just' or 'direct' is used.

It will be understood that, although the terms "first", "second", etc. may be used herein to describe various elements, these elements should not be limited by these terms. These terms are only used to distinguish one element from another. For example, a first element could be termed a second element, and, similarly, a second element could be termed a first element, without departing from the scope of the present invention.

Features of various embodiments of the present invention may be partially or overall coupled to or combined with each other, and may be variously inter-operated with each other and driven technically as those skilled in the art can sufficiently understand. The embodiments of the present invention may be carried out independently from each other, or may be carried out together in co-dependent relationship.

Hereinafter, embodiments of the present invention will be described in detail with reference to the accompanying drawings.

Figure 2:
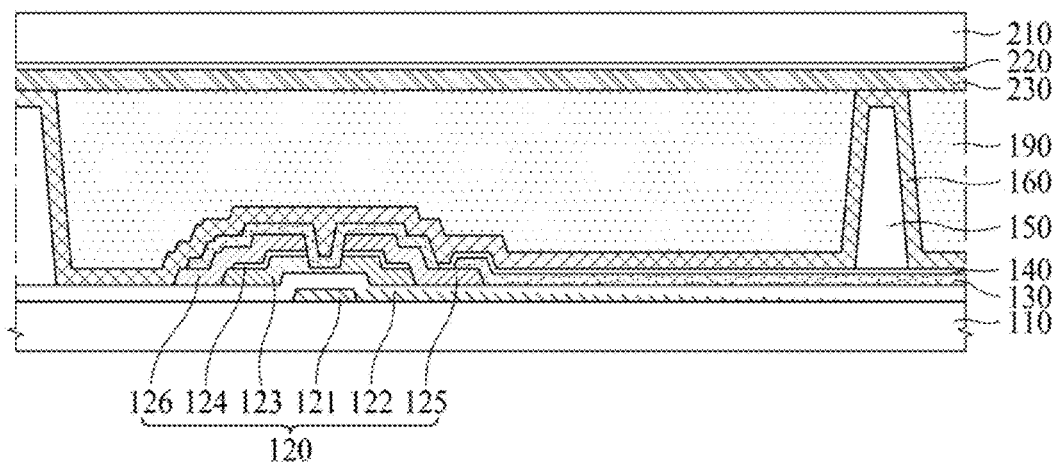
FIG. 2 is a cross-sectional view of a transparent display device according to an embodiment of the present invention.

FIG. 2 is a diagram illustrating a transparent display device 100 according to an embodiment of the present invention.

Referring to FIG. 2, the transparent display device 100 according to an embodiment of the present invention may include a first substrate 110 and a second substrate 210.

The first substrate 110 may include a thin film transistor (TFT) 120, a passivation layer 130, a first transparent electrode 140, a separation wall 150, and an electrochromic layer 160. The second substrate 210 may include a second transparent electrode 220 and a counter layer 230. Also, an electrolyte layer 190 may be disposed between the first substrate 110 and the second substrate 210. The electrochromic layer 160, the electrolyte layer 190, and the counter layer 230 may each be defined as an electrochromic element.

The first substrate 110 and the second substrate 210 may each be a transparent material or a plastic film. For example, each of the first substrate 110 and the second substrate 210 may be a sheet or a film which includes cellulose resin such as triacetyl cellulose (TAC), diacetyl cellulose (DAC), or the like, cyclo olefin polymer (COP) such as orbornene derivatives or the like, acrylic resin such as cyclo olefin copolymer (COC), poly(methylmethacrylate) (PMMA), or the like, polyolefin such as polycarbonate (PC), polyethylene (PE), polypropylene (PP), or the like, polyester such as polyvinyl alcohol (PVA), poly ether sulfone (PES), polyetheretherketone (PEEK), polyetherimide (PEI), polyethylenenaphthalate (PEN), polyethyleneterephthalate (PET), or the like, polyimide (PI), polysulfone (PSF), fluoride resin, and/or the like, but is not limited thereto.

The TFT 120 may include a gate electrode 121, a gate insulation layer 122, a semiconductor layer 123, an ohmic layer 124, a source electrode 125, and a drain electrode 126.

A metal material may be deposited on the first substrate 110, and a photoresist may be deposited on the metal material. Subsequently, a mask process where an exposure process, a development process, and an etching process are sequentially performed may be performed by using a mask (not shown), thereby forming the gate electrode 121.

Moreover, although not shown, a gate line connected to the gate electrode 121 may be formed simultaneously in the process of forming the gate electrode 121. Here, the gate electrode 121 may be formed by depositing one metal material, or may be formed by depositing two metal materials.

The gate insulation layer 122 may be disposed on a top of the first substrate 110 and may cover one surface of the gate electrode 121. Here, the gate insulation layer 122 may be formed through a plasma enhanced chemical vapor deposition (PECVD) process.

The semiconductor layer 123 may include amorphous silicon (a-Si) or crystalline silicon. The ohmic layer 124 included in the TFT 120 may be formed by adding P-type or N-type impurities into the amorphous silicon or the crystalline silicon. The semiconductor layer 123 may be ohmic-contacted with the source electrode 125 and the drain electrode 126 by the ohmic layer 124, thereby enhancing characteristic of the TFT 120.

The source electrode 125 and the drain electrode 126 included in the TFT 120 may be formed by following process. An electrode material is deposited on the semiconductor layer 123 and the electrode material is etched with a mask, thus the source electrode 125 and the drain electrode 126 may be formed.

The source electrode 125 may be electrically connected to the below-described first transparent electrode 140 through a contact hole. Accordingly, an image may be realized by transferring an electrical signal to the below-described electrochromic element.

The passivation layer 130 may be formed on the TFT 120, and in more detail, may be formed on a top of each of the source electrode 125 and the drain electrode 126. The passivation layer 130 protects the TFT 120. The passivation layer 130 may include an inorganic insulating material, for example, silicon oxide ($SiO_x$) or silicon nitride ($SiN_x$), but is not limited thereto. The passivation layer 130 may extend to the below-described electrochromic element.

The first transparent electrode 140 may be formed on a top of the passivation layer 130 and may be electrically connected to the source electrode 125. The passivation layer 130 may include a contact hole, and thus a voltage may be applied to the first transparent electrode 140. The first transparent electrode 140 may include silver oxide (for example, AgO, Ag$_2$O, or Ag$_2$O$_3$), aluminum oxide (for example, Al$_2$O$_3$), tungsten oxide (for example, WO$_2$, WO$_3$, or W$_2$O$_3$), magnesium oxide (for example, MgO), molybdenum oxide (for example, MoO$_3$), zinc oxide (for example, ZnO), tin oxide (for example, SnO$_2$), indium oxide (for example, In$_2$O$_3$), chromium oxide (for example, CrO$_3$ or Cr$_2$O$_3$), antimony oxide (for example, Sb$_2$O$_3$ or Sb$_2$O$_5$), titanium oxide (for example, TiO$_2$), nickel oxide (for example, NiO), copper oxide (for example, CuO or Cu$_2$O), vanadium oxide (for example, V$_2$O$_3$ or V$_2$O$_5$), cobalt oxide (for example, CoO), iron oxide (for example, Fe$_2$O$_3$ or Fe$_3$O$_4$), niobium oxide (for example, Nb2O5), indium tin oxide (for example, ITO), indium zinc oxide (for example, IZO), aluminum-doped zinc oxide (for example, ZAO), aluminum-doped tin oxide (for example, TAO), or antimony tin oxide (for example, ATO), but is not limited thereto.

The separation wall 150 may be disposed between the first transparent electrode 140 and the second transparent electrode 220 and may define a pixel of the transparent display device 100 according to an embodiment of the present invention. That is, the separation wall 150 may be disposed between adjacent pixels among a red pixel, a green pixel, and a blue pixel and may prevent mixing of the electrolyte layer 190. Also, the separation wall 190 may maintain a certain gap between the first substrate 110 and the second substrate 210.

The electrochromic layer 160 and the counter layer 230 may be formed over a top of the separation wall 150 as shown in FIG. 2, but is not limited thereto. For example, the electrochromic layer 160 may not be formed over the top of the separation wall 150 so that the separation wall 150 contacts the counter layer 230. Alternatively, the electrochromic layer 160 and the counter layer 230 may not be formed over the top of the separation wall 150 so that the separation wall 150 contacts the second transparent electrode 220.

The separation wall 150 may be formed of a transparent material. In this case, the separation wall 150 may be formed of one of photoresist, ultraviolet (UV)-curable polymer, and polydimethylsiloxane, but is not limited thereto.

The separation wall 150 may be narrowed in a direction from the electrochromic layer 160 to the counter layer 230, but is not limited thereto. For example, a width of the separation wall 150 may be constant, or may be narrowed progressively closer to the electrochromic layer 160.

A plan view of the separation wall 150 is not shown, but the separation wall 150 may have various shapes in the plan view thereof. For example, the separation wall 150 may have a stripe shape, a dot shape, a honeycomb shape, and/or the like, but is not limited thereto.

The electrochromic layer 160 may include an electrochromic material. When a reduction reaction is performed on the electrochromic material, the electrochromic material may absorb a certain color to have the certain color, and when an oxidation reaction is performed on the electrochromic material, the electrochromic material may be changed to a transparent material. For example, the electrochromic material according to an embodiment of the present invention may include a compound represented by the following Formula 1.

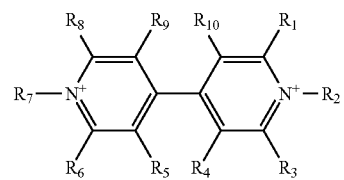

[Formula 1]

where R$_1$ to R$_{10}$ may be individually selected from hydrogen and a substituted or unsubstituted hydrocarbon. The hydrocarbon may be selected from the group consisting of an alkyl group, a cycloalkyl group, a polycycloalkyl group, a heterocycloalkyl group, an aryl group, an aralkyl group, an alkoxy group, an alkenyl group, and an alkynyl group. The hydrocarbon may be substituted by a group selected from aryl, halogens, nitrogen, oxygen, alcohols, esters, ammonium salts, or phosphonium salts.

As described above, the electrochromic layer 160 may realize a transparent mode where when a voltage is not applied to the first transparent electrode 140, an oxidation reaction is performed on the material of Formula 1, and thus, the material is changed to a transparent material. Also, when the voltage is applied to the first transparent electrode 140, a reduction reaction is performed on the material of Formula 1, and thus, the electrochromic layer 160 may have a certain color. In this case, the electrochromic layer 160 may have a certain color such as red, green, blue, or the like, based on a substituted material in R$_1$ to R$_{10}$ of Formula 1.

For example, the electrochromic layer 160 may include a compound represented by the following Formula 2 where the R$_2$ of Formula 1 is a methyl group, and the other R groups are hydrogen atoms. When a voltage is applied to the first transparent electrode 140, a reduction reaction may be performed on a material of the following Formula 2 to realize red.

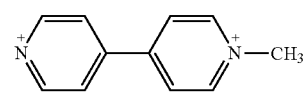

[Formula 2]

For example, the electrochromic layer 160 may include a compound represented by the following Formula 3 where the R$_2$ and R$_7$ of Formula 1 are each a pentyl group, and the other R groups are hydrogen atoms. When the voltage is applied to the first transparent electrode 140, a reduction reaction may be performed on a material of the following Formula 3 to realize green.

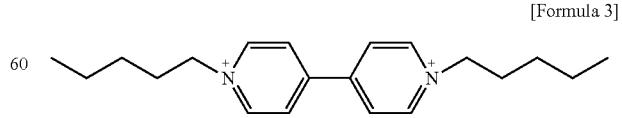

[Formula 3]

For example, the electrochromic layer 160 may include a compound represented by the following Formula 4 where the R$_2$ and R$_7$ of Formula 1 are each a phenyl group, and the other R groups are hydrogen atoms. When the voltage is applied to the first transparent electrode 140, a reduction reaction may be performed on a material of the following Formula 4 to realize blue.

[Formula 4]

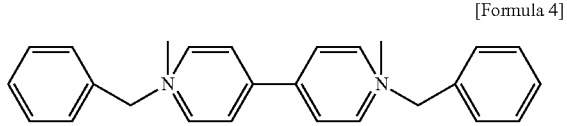

As described above, when the voltage is applied to the first transparent electrode 140, a reduction reaction may be performed on a material represented by each of Formulas 2 to 4, and thus, the electrochromic layer 160 may have a certain color. However, the present embodiment is not limited thereto. In other embodiments, the electrochromic layer 160 may include an electrochromic material for realizing a color other than red, green, and blue.

The electrolyte layer 190 may include an electrolyte, a polymer, and a UV initiator. The electrolyte may be, for example, lithium perchlorate, t-butylammoinum perchlorate, t-butylammoinum-t-fluoroborate, tetrabutylammonium trifluoromethanesulfonate, or the like. The polymer may be, for example, a polyacrylate-based polymer, a polyester-based polymer, an epoxy-based polymer, or the like. The UV initiator may be, for example, benzoinethers, amines, or the like. The electrolyte layer 190 may supply a positive ion and a negative ion in order for the electrochromic layer 160 and the counter layer 230 to perform an oxidation-reduction reaction.

The second transparent electrode 220 on the second substrate 210 may be formed all over the second substrate 210 and may include a material which is the same as that of the first transparent electrode 140. The second transparent electrode 210 may include silver oxide (for example, AgO, $Ag_2O$, or $Ag_2O_3$), aluminum oxide (for example, $Al_2O_3$), tungsten oxide (for example, $WO_2$, $WO_3$, or $W_2O_3$), magnesium oxide (for example, MgO), molybdenum oxide (for example, $MoO_3$), zinc oxide (for example, ZnO), tin oxide (for example, $SnO_2$), indium oxide (for example, $In_2O_3$), chromium oxide (for example, $CrO_3$ or $Cr_2O_3$), antimony oxide (for example, $Sb_2O_3$ or $Sb_2O_5$), titanium oxide (for example, $TiO_2$), nickel oxide (for example, NiO), copper oxide (for example, CuO or $Cu_2O$), vanadium oxide (for example, $V_2O_3$ or $V_2O_5$), cobalt oxide (for example, CoO), iron oxide (for example, $Fe_2O_3$ or $Fe_3O_4$), niobium oxide (for example, $Nb_2O_5$), indium tin oxide (for example, ITO), indium zinc oxide (for example, IZO), aluminum-doped zinc oxide (for example, ZAO), aluminum-doped tin oxide (for example, TAO), or antimony tin oxide (for example, ATO), but is not limited thereto.

The counter layer 230 may be provided on one surface of the second transparent electrode 220 to face the first substrate 110. The counter layer 230 may be a layer that helps an oxidation-reduction reaction to be smoothly performed on the electrochromic layer 160. When an oxidation reaction is performed on the counter layer 230, the counter layer 230 may absorb a certain color to have a certain color. Also, the counter layer 230 may include a counter material which is changed to a transparent material by the reduction reaction. However, the counter layer 230 may be omitted. Also, the counter layer 230 may include a compound represented by the following Formula 5.

[Formula 5]

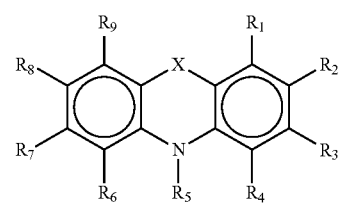

where X may be $-NR_{10}-$, $-O-$, or $-S-$, and $R_1$ to $R_{10}$ may be individually selected from hydrogen and a substituted or unsubstituted hydrocarbon. The hydrocarbon may be selected from the group consisting of an alkyl group, a cycloalkyl group, a polycycloalkyl group, a heterocycloalkyl group, an aryl group, an aralkyl group, an alkoxy group, an alkenyl group, and an alkynyl group. The hydrocarbon may be substituted by a group selected from aryl, halogens, nitrogen, oxygen, alcohols, esters, ammonium salts, or phosphonium salts.

The counter layer 230 and the electrochromic layer 160 may have the following relationship. If an oxidation reaction is performed on the counter layer 230, a reduction reaction may be performed on the electrochromic layer 160, and if a reduction reaction is performed on the counter layer 230, an oxidation reaction may be performed on the electrochromic layer 160.

Figure 3:
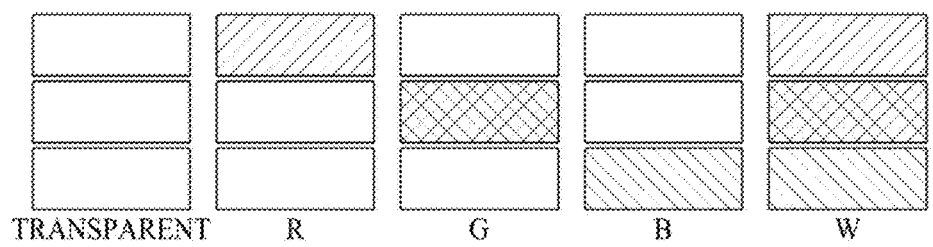
FIG. 3 is a plan view of a pixel operation of a transparent display device according to an embodiment of the present invention.

FIG. 3 is a diagram illustrating a pixel operation of the transparent display device 100 according to an embodiment of the present invention.

Referring to FIG. 3, the transparent display device 100 according to an embodiment of the present invention may operate in a transparent mode and a display mode.

That is, when a voltage is applied to the first transparent electrode 140 and the second transparent electrode 220, an electrochemical oxidation-reduction reaction may be performed on the counter layer 230 and the electrochromic layer 160, and thus, a color of each of the counter layer 230 and the electrochromic layer 160 may be changed.

For example, when a positive voltage is applied to the first transparent electrode 140 and a negative voltage is applied to the second transparent electrode 220, a reduction reaction may be performed on the electrochromic layer 160, and an oxidation reaction may be performed on the counter layer 230. In this manner, the electrochromic layer 160 may have a certain color due to the reduction reaction, thereby realizing the display mode where an image is displayed.

Moreover, when a negative voltage is applied to the first transparent electrode 140 and a positive voltage is applied to the second transparent electrode 220, a reduction reaction may be performed on the counter layer 230, and an oxidation reaction may be performed on the electrochromic layer 160. In this manner, the electrochromic layer 160 may be transparently changed by the oxidation reaction, thereby realizing the transparent mode.

In the transparent display device 100 according to an embodiment of the present invention, when an image is displayed in the display mode, a transmittance may be controlled by adjusting a driving voltage. That is, the display mode where an image is displayed and the transparent mode where an object located on a backside is shown without an image being displayed may be performed simultaneously. Also, in a state where a voltage is not applied, the transparent display device 100 may have a transmittance of about 70% to about 90% and an image color change speed of 100 msec or less. That is, in the transparent display device 100 according to an embodiment of the present invention, since a polarizing film is removed unlike the related art transparent display device, a higher transmittance is realized, and a transparent area wider than a TFT area is secured for each pixel. Accordingly, in the transparent display device 100 according to an embodiment of the present invention, a high transmittance is secured in the transparent mode.

Figure 4:
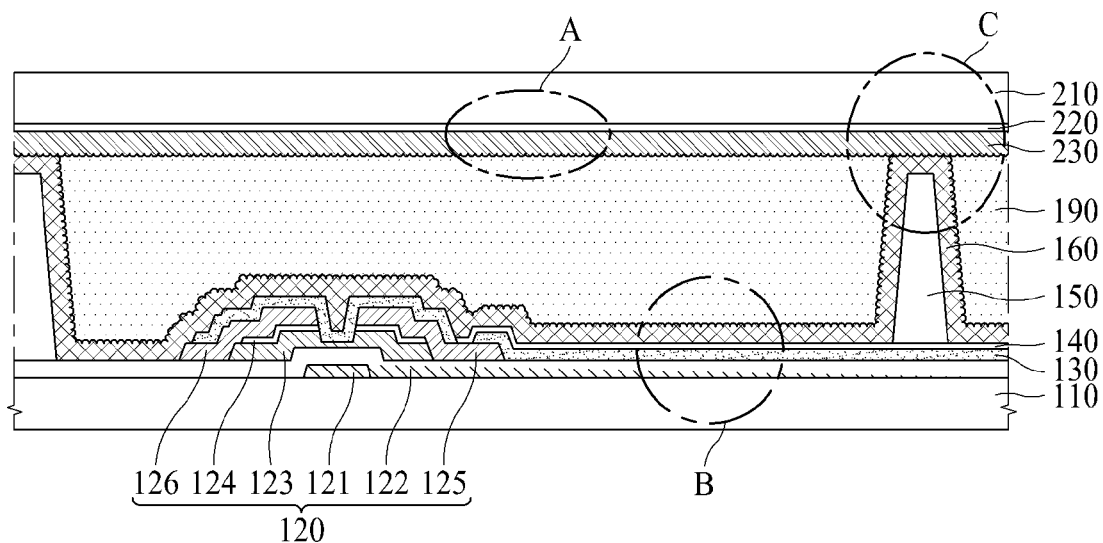
FIG. 4 is a cross-sectional view of a transparent display device according to another embodiment of the present invention.
Figure 5:
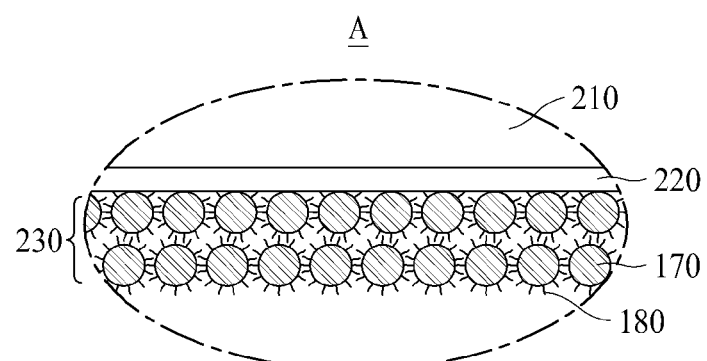
FIG. 5 is an expanded view of area A of the transparent display device illustrated in FIG. 4.
Figure 6:
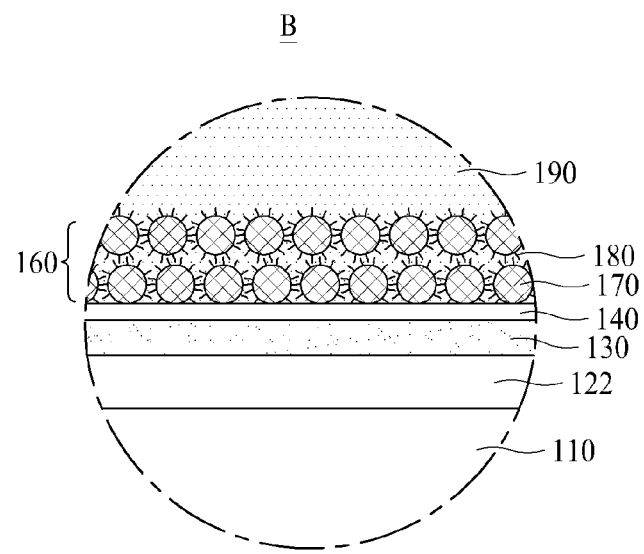
FIG. 6 is an expanded view of area B of the transparent display device illustrated in FIG. 4.
Figure 7:
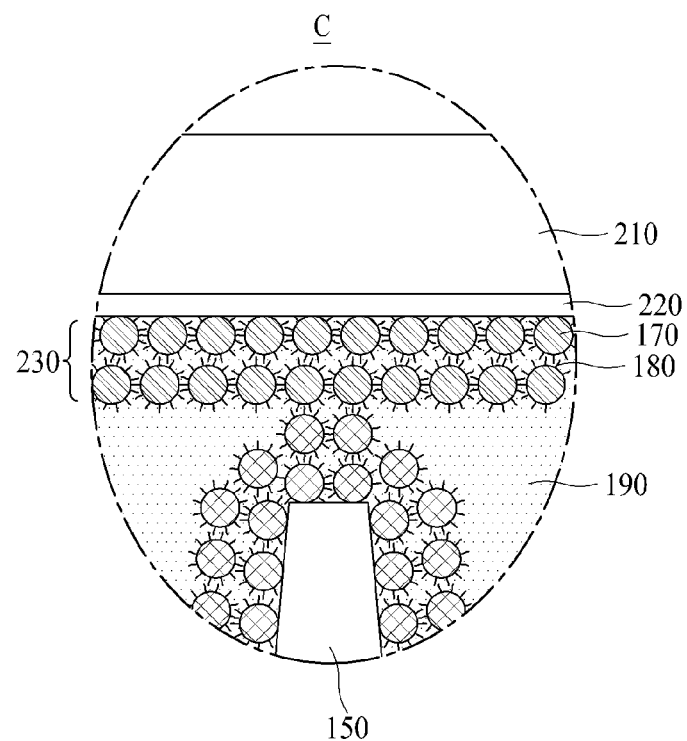
FIG. 7 is an expanded view of area C of the transparent display device illustrated in FIG. 4.

FIG. 4 is a diagram illustrating a transparent display device 100 according to another embodiment of the present invention. FIG. 5 is a diagram illustrating an area A illustrated in FIG. 4. FIG. 6 is a diagram illustrating an area B illustrated in FIG. 4. FIG. 7 is a diagram illustrating an area C illustrated in FIG. 4.

The transparent display device 100 of FIG. 4 has been implemented by modifying some elements of the transparent display device 100 illustrated in FIGS. 2 and 3, and thus, descriptions of repetitive elements are not repeated.

Referring to FIG. 4, in the transparent display device 100 according to another embodiment of the present invention, a core material 170 such as transparent conductive oxide (TCO) or the like and an electrochromic material 180 combined with the core material 170 may be included in an electrochromic layer 160 and a counter layer 230. The core material 170 may be a material which is obtained by surface-treating $TiO_2$ on $TiO_2$, $In_2O_3$, $SnO_2$, $RuO_2$, or ITO.

Referring to FIGS. 5 to 7, the core material 170 may be provided on one surface of each of first and second transparent electrodes 140 and 220 and a passivation layer 130. The core material 170 may be in the form of spherical particles. The electrochromic material 180 may cling to surfaces of the spherical particles. The core material 170 is illustrated as configuring two layers in the drawing, but this is for convenience of description. The present embodiment is not limited thereto.

The electrochromic material 180 clinging to a surface of the core material 170 may include the above-described materials of Formulas 1 to 5. Further, the electrochromic layer 160 may include the materials of Formulas 1 to 4, and the counter layer 230 may include the material of Formula 5.

In detail, the core material 170 may be defined by the functional groups $R_1$ to $R_{10}$ represented in Formulas 1 to 5, and the electrochromic material 180 may be a viologen (a salt including two pyridinyl groups) represented in Formulas 1 to 4.

In addition to the features of the transparent display device 100 according to an embodiment of the present invention, the transparent display device 100 according to another embodiment of the present invention has a feature where since the electrochromic material 180 clinging to the surface of the core material 170 and thus is changed in color, a time taken in changing a color through diffusion is reduced, and thus, a color is changed at a super-high speed.

As described above, according to the embodiments of the present invention, provided is a transparent display device which realizes a high resolution when displaying an image in the display mode.

Moreover, according to the embodiments of the present invention, provided is a transparent display device which realizes a transmittance of 50% or more in a transparent mode.

Moreover, according to the embodiments of the present invention, provided is a transparent display device which changes a color at a high speed when displaying an image in the display mode.

It will be apparent to those skilled in the art that various modifications and variations can be made in the present invention without departing from the spirit or scope of the inventions. Thus, it is intended that the present invention covers the modifications and variations of this invention provided they come within the scope of the appended claims and their equivalents.

What is claimed is:

1. A transparent display device comprising:
a first substrate and a second substrate facing each other;
a thin film transistor (TFT) disposed on one surface of the first substrate;
a first transparent electrode connected to the TFT;
a second transparent electrode disposed on the second substrate to face the first substrate; and
an electrochromic element provided between the first transparent electrode and the second transparent electrode.

2. The transparent display device of claim 1, wherein:
the TFT comprises a source electrode and a passivation layer disposed on the source electrode, and
the source electrode transfers an electrical signal to the first transparent electrode through a contact hole included in the passivation layer.

3. The transparent display device of claim 1, wherein the electrochromic element comprises:
an electrochromic layer provided on the first transparent electrode;
a counter layer provided on the second transparent electrode to face the first substrate; and
an electrolyte layer disposed between the electrochromic layer and the counter layer.

4. The transparent display device of claim 3, wherein the electrochromic layer comprises one of a material emitting red light, a material emitting green light, and a material emitting blue light.

5. The transparent display device of claim 4, wherein the electrochromic layer comprises a compound represented by Formula 1:

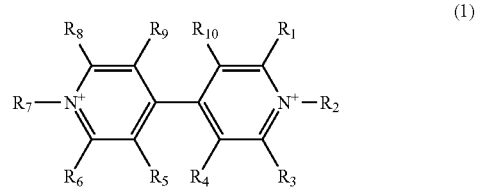

(1)

wherein $R_1$ to $R_{10}$ is individually selected from hydrogen and a substituted or unsubstituted hydrocarbon, and wherein the hydrocarbon is selected from the group consisting of an alkyl group, a cycloalkyl group, a polycycloalkyl group, a heterocycloalkyl group, an aryl group, an aralkyl group, an alkoxy group, an alkenyl group, and an alkynyl group.

6. The transparent display device of claim 5, wherein the hydrocarbon is substituted by a group selected from aryl groups, halogen, nitrogen, oxygen, alcohols, esters, ammonium salts, or phosphonium salts.

7. The transparent display device of claim 4, wherein the electrochromic layer comprises a compound represented by Formula 2:

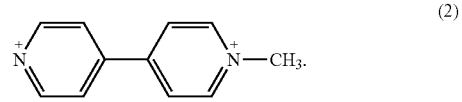

(2)

8. The transparent display device of claim 4, wherein the electrochromic layer comprises a compound represented by Formula 3:

(3)

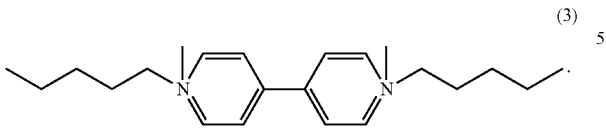

9. The transparent display device of claim 4, wherein the electrochromic layer comprises a compound represented by Formula 4:

(4)

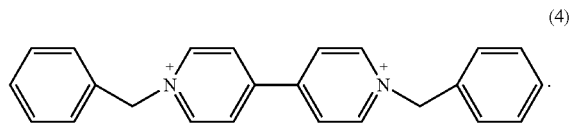

10. The transparent display device of claim 4, wherein the counter layer comprises a compound represented by Formula 5:

(5)

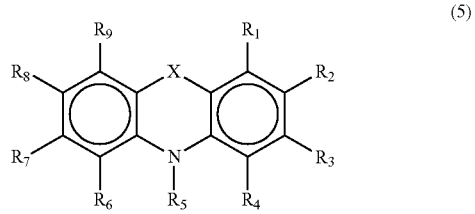

wherein X is selected from $-NR_{10}-$, $-O-$ and $-S-$, and $R_1$ to $R_{10}$ is individually selected from hydrogen and a substituted or unsubstituted hydrocarbon, and wherein the hydrocarbon is selected from the group consisting of an alkyl group, a cycloalkyl group, a polycycloalkyl group, a heterocycloalkyl group, an aryl group, an aralkyl group, an alkoxy group, an alkenyl group, and an alkynyl group.

11. The transparent display device of claim 10, wherein the hydrocarbon is substituted by a group selected from aryl groups, halogens, nitrogen, oxygen, alcohols, esters, ammonium salts, or phosphonium salts.

12. The transparent display device of claim 3, wherein the electrochromic layer is oxidized, and the counter layer is reduced to produce a color.

13. The transparent display device of claim 3, wherein the electrochromic layer is reduced to produce a color, and the counter layer is oxidized.

14. The transparent display device of claim 3, further comprising a separation wall dividing a red pixel area, a green pixel area, and a blue pixel area.

15. The transparent display device of claim 3, wherein, when a voltage is not applied, the transparent display device has a transmittance of about 70% to about 90%.

16. The transparent display device of claim 3, wherein, when a voltage is not applied, the transparent display device has an image color change speed of 100 msec or less.

\* \* \* \* \*